United States Patent
Wu et al.

(10) Patent No.: US 7,466,793 B2
(45) Date of Patent: Dec. 16, 2008

(54) DISTINCT INCIDENT ENERGY SPECTRA DETECTION

(75) Inventors: Xiaoye Wu, Rexford, NY (US); James W. LeBlanc, Niskayuna, NY (US); Samit Kumar Basu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 61 days.

(21) Appl. No.: 11/553,411

(22) Filed: Oct. 26, 2006

(65) Prior Publication Data

US 2008/0101535 A1    May 1, 2008

(51) Int. Cl.
    *G01N 23/00*  (2006.01)
(52) U.S. Cl. .................................. 378/19; 378/4; 378/5
(58) Field of Classification Search ...................... 378/4, 378/9, 207, 901, 19, 5
    See application file for complete search history.

(56) References Cited

U.S. PATENT DOCUMENTS

| | | | |
|---|---|---|---|
| 6,341,154 B1 * | 1/2002 | Besson ........................ | 378/15 |
| 6,813,333 B2 | 11/2004 | Karau et al. | |
| 6,891,918 B2 | 5/2005 | Drummond et al. | |
| 7,254,259 B2 * | 8/2007 | Hsieh et al. .................. | 382/131 |
| 7,272,429 B2 * | 9/2007 | Walker et al. ................ | 600/407 |
| 2002/0122528 A1 * | 9/2002 | Besson .......................... | 378/4 |
| 2005/0173641 A1 * | 8/2005 | Unger et al. ........... | 250/370.09 |
| 2006/0018423 A1 * | 1/2006 | Bruder et al. .................. | 378/9 |
| 2006/0193430 A1 * | 8/2006 | Kuhn ............................ | 378/9 |

OTHER PUBLICATIONS

Definition of "Beam hardening" from Medcyclopedia.com.

* cited by examiner

*Primary Examiner*—Courtney Thomas
*Assistant Examiner*—Alexander H Taningco
(74) *Attorney, Agent, or Firm*—Jason K. Klindtworth (57) ABSTRACT

A CT system in an example comprises one or more high frequency electromagnetic energy sources, a detection assembly, a data acquisition system (DAS), and a computer. The one or more high frequency electromagnetic energy sources emit one or more beams of high frequency electromagnetic energy toward an object to be imaged. The detection assembly is capable of measuring a plurality of projection data at a same projection path that corresponds to a plurality of distinct incident energy spectra. The detection assembly comprises one or more energy discriminating (ED) detectors and/or one or more energy integration (EI) detectors that receive high frequency electromagnetic energy emitted by the one or more high frequency electromagnetic energy sources. The data acquisition system (DAS) is operably connected to the one or more ED detectors and/or the one or more EI detectors. The computer is operably connected to the DAS.

12 Claims, 4 Drawing Sheets

DISTINCT INCIDENT ENERGY SPECTRA DETECTION

BACKGROUND OF THE INVENTION

The present invention relates generally to diagnostic imaging and, more particularly, to a method and apparatus of recovering missing projection data in an energy discrimination (ED) diagnostic imaging system.

Exemplary diagnostics devices comprise x-ray systems, magnetic resonance (MR) systems, ultrasound systems, computed tomography (CT) systems, positron emission tomography (PET) systems, and other types of imaging systems. It is well-understood that in medical imaging, it is necessary to measure the same attenuation path at least two times with different incident x-ray spectra, in order to obtain material specific information. Exemplary approaches to create distinct incident spectra for an energy discrimination CT system comprise: (i) image the same object at different tube kilovoltage potentials (kVp's); (ii) employ an energy sensitive detector to divide the same incident energy spectrum into several sub spectra; (iii) use a layered detector assembly such that each detector layer senses a different x-ray energy spectrum. Such CT systems have the ability to compute the conventional Hounsfield Unit (HU) value as well as a certain level of information about the material composition. The information about object material composition is typically obtained through "basis material decomposition (BMD)." In exemplary BMD, the measured dual-spectral projection data are re-mapped to the integrated density projection data corresponding to two basis materials.

Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

An exemplary implementation of a CT system comprises an energy integrating (EI) CT system. In the EI CT system, the detector gets a charge that is proportional to the integral of the area of the pixel exposed to the x-ray beam, the time of exposure, and the integral of the energy weighted spectra that hit the pixel. The EI detector integrates these three things simultaneously and gives a single charge that is then converted into a CT image.

Another exemplary implementation of a CT system comprises an energy discriminating (ED) CT system. Exemplary photon counting and ED detectors have limited count rate. Below the limited count rate, the ED detector can record the energy of the incident photons, or the integral counts corresponding to a given energy region, often call an "energy bin". There could be multiple energy bins provided by an ED detector, each of which covers a targeted energy region of the incident x-ray photons. To use these detectors for medical or other high-flux CT applications, the CT system has to deal with the loss of ED detector readouts, where the incoming x-ray photon count rate exceeds the limit of the ED detectors.

Another exemplary implementation of a CT system comprises main and secondary detectors, each with an associated x-ray tube. The main detector covers the field of view (FOV), while the secondary detector has a limited FOV. This system improves the temporal resolution while the tubes are operated at the same kVp. The missing data in the secondary detector are patched with the data from the main detector. To operate the tube at different kVp's for material decomposition, the missing data in the secondary detector cannot be patched directly with the data from the main detector, due to the kVp inconsistency. The effective FOV with the dual-kVp technique is restricted by the secondary detector, since the data recovery algorithm provides an inadequate patch.

Therefore, it would be desirable to promote a decrease in effects of limitations of photon counting in an ED diagnostic imaging system.

BRIEF DESCRIPTION OF THE INVENTION

The invention in an implementation encompasses a CT system. The CT system comprises one or more high frequency electromagnetic energy sources, a detection assembly, a data acquisition system (DAS), and a computer. The one or more high frequency electromagnetic energy sources emit one or more beams of high frequency electromagnetic energy toward an object to be imaged. The detection assembly is capable of measuring a plurality of projection data at a same projection path that corresponds to a plurality of distinct incident energy spectra. The detection assembly comprises one or more energy discriminating (ED) detectors and/or one or more energy integration (EI) detectors that receive high frequency electromagnetic energy emitted by the one or more high frequency electromagnetic energy sources. The data acquisition system (DAS) is operably connected to the one or more ED detectors and/or the one or more EI detectors. The computer is operably connected to the DAS.

Another implementation of the invention encompasses a CT system. The CT system comprises a detection assembly, a data acquisition system (DAS), and a computer. The detection assembly is capable of measuring a plurality of projection data at a same projection path that corresponds to a plurality of distinct incident energy spectra. The detection assembly comprises one or more energy discriminating (ED) detectors and/or one or more energy integration (EI) detectors that receive high frequency electromagnetic energy emitted by one or more high frequency electromagnetic energy sources that emit one or more beams of high frequency electromagnetic energy toward an object to be imaged. The data acquisition system (DAS) is operably connected to the one or more ED detectors and/or the one or more EI detectors. The computer is operably connected to the DAS and programmed to: patch missing data of the plurality of projection data at the same projection path in an incident energy spectrum of the plurality of distinct incident energy spectra.

A further implementation of the invention encompasses a CT system. The CT system comprises a detection assembly, a data acquisition system (DAS), and a computer. The detection assembly is capable of measuring a plurality of projection data at a same projection path that corresponds to a plurality of distinct incident energy spectra. The detection assembly comprises one or more energy discriminating (ED) detectors and/or one or more energy integration (EI) detectors that receive high frequency electromagnetic energy emitted by one or more high frequency electromagnetic energy sources that emit one or more beams of high frequency electromagnetic energy toward an object to be imaged. The data acquisition system (DAS) is operably connected to the one or more ED detectors and/or the one or more EI detectors. The computer is operably connected to the DAS and programmed to: patch missing data of the plurality of projection data at the same projection path through employment of a correlation function between two or more projections acquired at different spectra.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Exemplary diagnostics devices comprise x-ray systems, magnetic resonance (MR) systems, ultrasound systems, computed tomography (CT) systems, positron emission tomography (PET) systems, and other types of imaging systems. Exemplary applications of x-ray sources comprise imaging, medical, security, and industrial inspection applications. The operating environment of an exemplary implementation comprises a 64-slice CT system. However, it will be appreciated by those skilled in the art that an exemplary implementation is applicable for use with single-slice or other multi-slice configurations. Moreover, an exemplary implementation is employable for the detection and conversion of x-rays. However, one skilled in the art will further appreciate that an exemplary implementation is employable for the detection and conversion of other high frequency electromagnetic energy. An exemplary implementation is employable with a "third generation" CT scanner and/or other CT systems.

Figure 1:
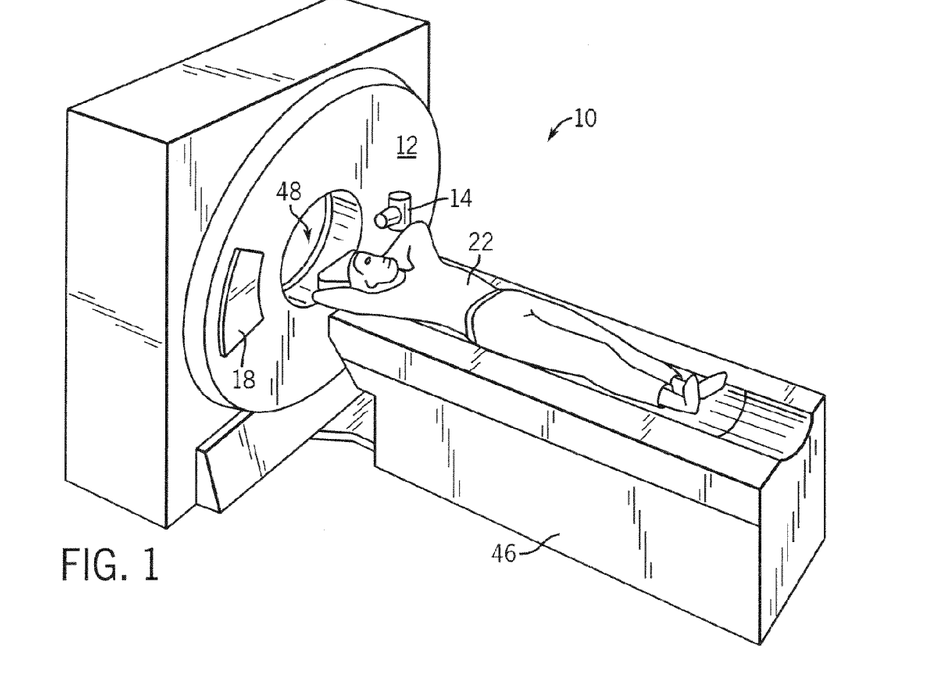
FIG. 1 is a pictorial view of a CT imaging system.
Figure 2:
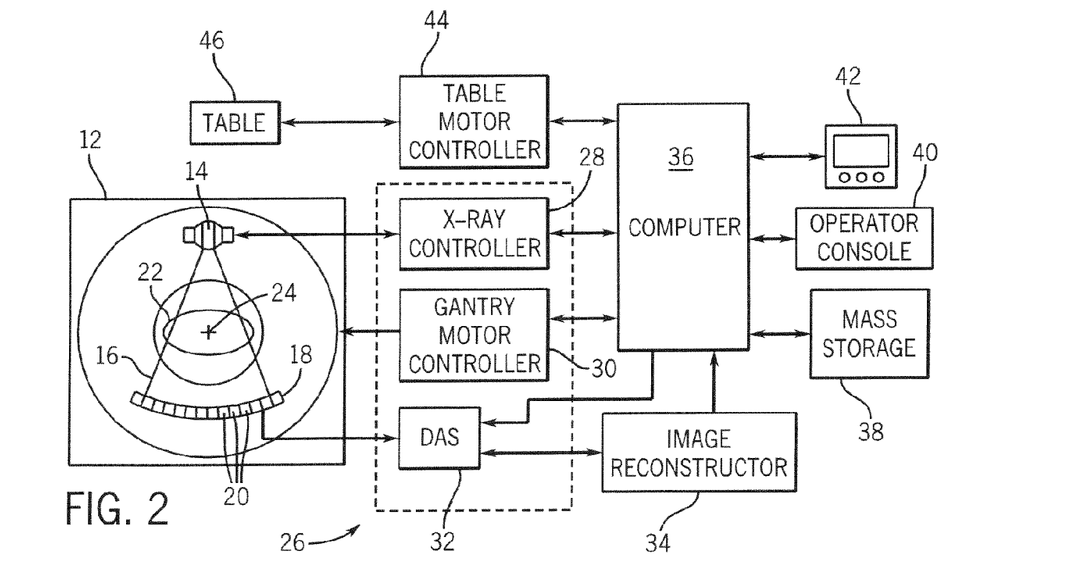
FIG. 2 is a block schematic diagram of the system illustrated in FIG. 1.
Figure 3:
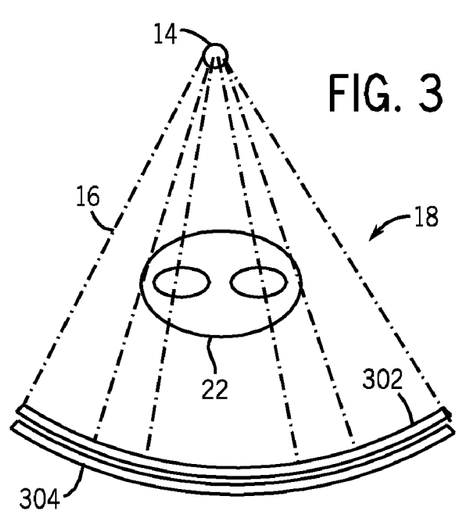
FIG. 3 is a partial, cutaway, schematic representation of an exemplary detector that comprises an energy discriminating (ED) detector and an energy integrating (EI) detector in a detector arrangement that receives a beam of high frequency electromagnetic energy in the system of FIG. 1.

Referring to FIGS. 1-3, a computed tomography (CT) imaging system 10 is shown as including a gantry 12 representative of a "third generation" CT scanner. The CT imaging system 10 in an example comprises a hybrid CT imaging system that comprises an energy discriminating (ED) detector 302 and an energy integrating (EI) detector 304, as a detector arrangement and/or detection assembly 18. Gantry 12 has an x-ray source 14 that projects a beam of x-rays 16 toward the detection assembly 18 on the opposite side of the gantry 12. Detection assembly 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. The detectors 20 in an example are arranged in the ED detector 302 and the EI detector 304, for example, in respective arrays. Additional exemplary description of the detection assembly 18 is presented herein. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

FIG. 3 is a partial, cutaway, schematic representation of the ED detector 302 and the EI detector 304 in the detection assembly 18 that receives a beam of high frequency electromagnetic energy. The ED detector 302 in an example is located upstream of the EI detector 304 in receiving the beam of x-rays 16. The ED detector 302 is located upstream of the EI detector 304 for receipt of the beam of x-rays 16. For example, location of the ED detector 302 upstream of the EI detector 304 serves to allow the ED detector 302 to have non-attenuated content, including low-energy content, from the beam of x-rays 16. In another example, the ED detector 302 is located downstream of the EI detector 304 in receiving the beam of x-rays 16. The ED detector 302 and the EI detector 304 are substantially adjacent and coextensive for receipt of the beam of x-rays 16. Electronics for the ED detector 302 and/or the EI detector 304 may be mounted axially and/or radially.

Figure 4:
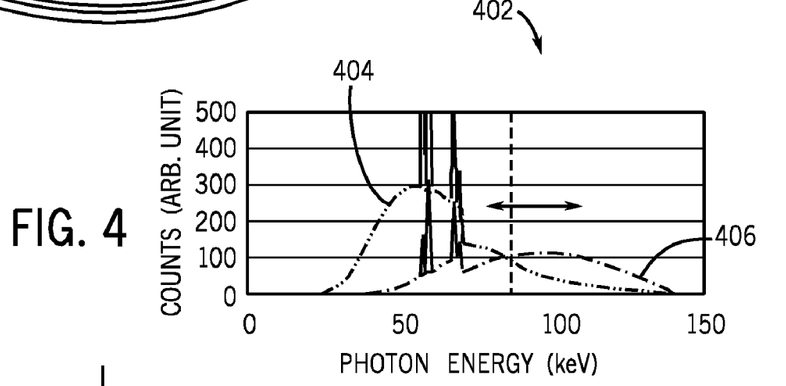
FIG. 4 is an exemplary plot of a high frequency electromagnetic energy spectrum received by the ED detector and a high frequency electromagnetic energy spectrum received by the EI detector from the beam of high frequency electromagnetic energy such as in FIG. 3.
Figure 5:
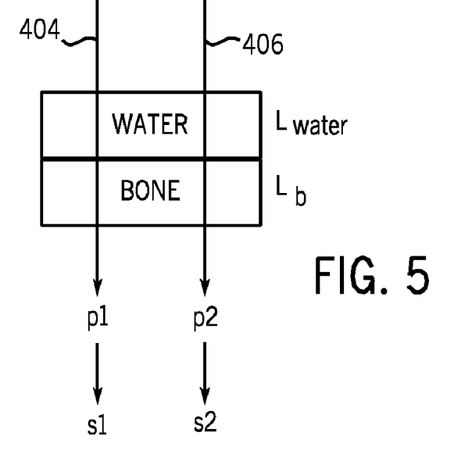
FIG. 5 represents the high frequency electromagnetic energy spectra such as from FIG. 4 passing through exemplary materials.

Referring to FIG. 4, exemplary plot 402 illustrates a high frequency electromagnetic energy spectrum received by the ED detector 302 and a high frequency electromagnetic energy spectrum received by the EI detector 304 from the beam of high frequency electromagnetic energy. The exemplary plot 402 illustrates x-ray spectrum 404 received by the ED detector 302 from the beam of x-rays 16 and x-ray spectrum 406 received by the EI detector 304 from the beam of x-rays 16. The spectral distribution in an example is determined by a voltage potential placed on x-ray tubes of the x-ray source 14 and current applied to drive the x-ray tubes of the x-ray source 14.

The ED detector 302 in an example obtains ED readout from the beam of x-rays 16. The EI detector 304 in an example obtains the EI readout from the beam of x-rays 16. An exemplary implementation obtains the EI readout of the projection simultaneously with the ED readout, or in the absence of the ED readout. The readout from the EI 304 detector in an example is employed to patch the corresponding projections in any individual ED energy bin, where the ED detector 302 saturates.

The ED detector 302 and the EI detector 304 perform substantially simultaneous measurements of the beam of x-rays 16. In an exemplary normal operating condition, the ED detector 302 records the energy of each incoming photon, and increases the counts in the proper energy bin where the energy of the photon falls. There could be several energy bins that each covers a limited energy range. An exemplary output of the ED detector 302 comprises an integrated number of photons corresponding to a specific and/or targeted energy region of the incident spectrum. The ED detector 302 is unable to measure all the data possible from the beam of x-rays 16 because of photon saturation. The EI detector 304 does measure all the data possible for the EI detector 304 from the beam of x-rays 16 after passing through the ED detector 302.

The saturation of the ED detector 302 in the low energy part of the spectrum of the beam of x-rays 16 causes the ED detector 302 alone to miss part of the data. The EI detector 304 complements the ED detector 302 to substantially and/or partially compensate for, measure, and/or recover the data missed by the ED detector 302. Without the assistance of the EI detector 304, the ED detector 302 would provide data that result in image artifacts. For example, the assistance by the EI detector 304 for the ED detector 302 serves to reduce demands in management of the photon flux.

An exemplary approach serves to recover lost data, for example, count data saturation, in the ED detector 302 in a hybrid EDCT system as the CT system 10, or missing projection data in a secondary detector (not shown), or other CT systems, where only partial projections are measured for one incident energy spectrum. The exemplary approach serves compute the missing projection data by transforming corresponding projections measured at another incident energy spectrum. The transformation is through a correlation function, as will be appreciated by those skilled in the art.

In medical x-ray CT, body material components and the commonly used contrast agent iodine can be represented by the combination of two materials; these two materials are called basis materials. The bases in an example comprise any two materials free of k-edge absorption in the effective energy region covered by the beam of x-rays 16. Water and bone in an example serve as the bases. An exemplary energy discrimination CT system measures the same projection path with at least two distinct incident x-ray spectra, providing corresponding projection data (p1, p2), where p1 and p2 in an example comprise the logarithmic result of the ratio of the measurements without and with the object in the beam. The projection data (p1, p2) are spectrally corrected to yield projection data (s1, s2), as will be appreciated by those skilled in the art. The projection data s1 and s2 comprise projection data corresponding to different incident spectra, but at the same path. The projection data s1 and s2 are linearized to the thickness of water.

Material decomposition methods may be applied to data pair (s1, s2), resulting in a new data pair (L1, L2), where L1 and L2 are the integrated densities of the basis material along the same projection path as original projections s1 or s2. Among the data set (s1, s2, L1, L2), only two parameters are independent. Thus, one can always find a functional for F( ) which has the property of: s1=F(s2, Lb). Lb comprises projection content of one basis material in the data pair (L1, L2). For example, Lb corresponds to bone.

Figure 6:
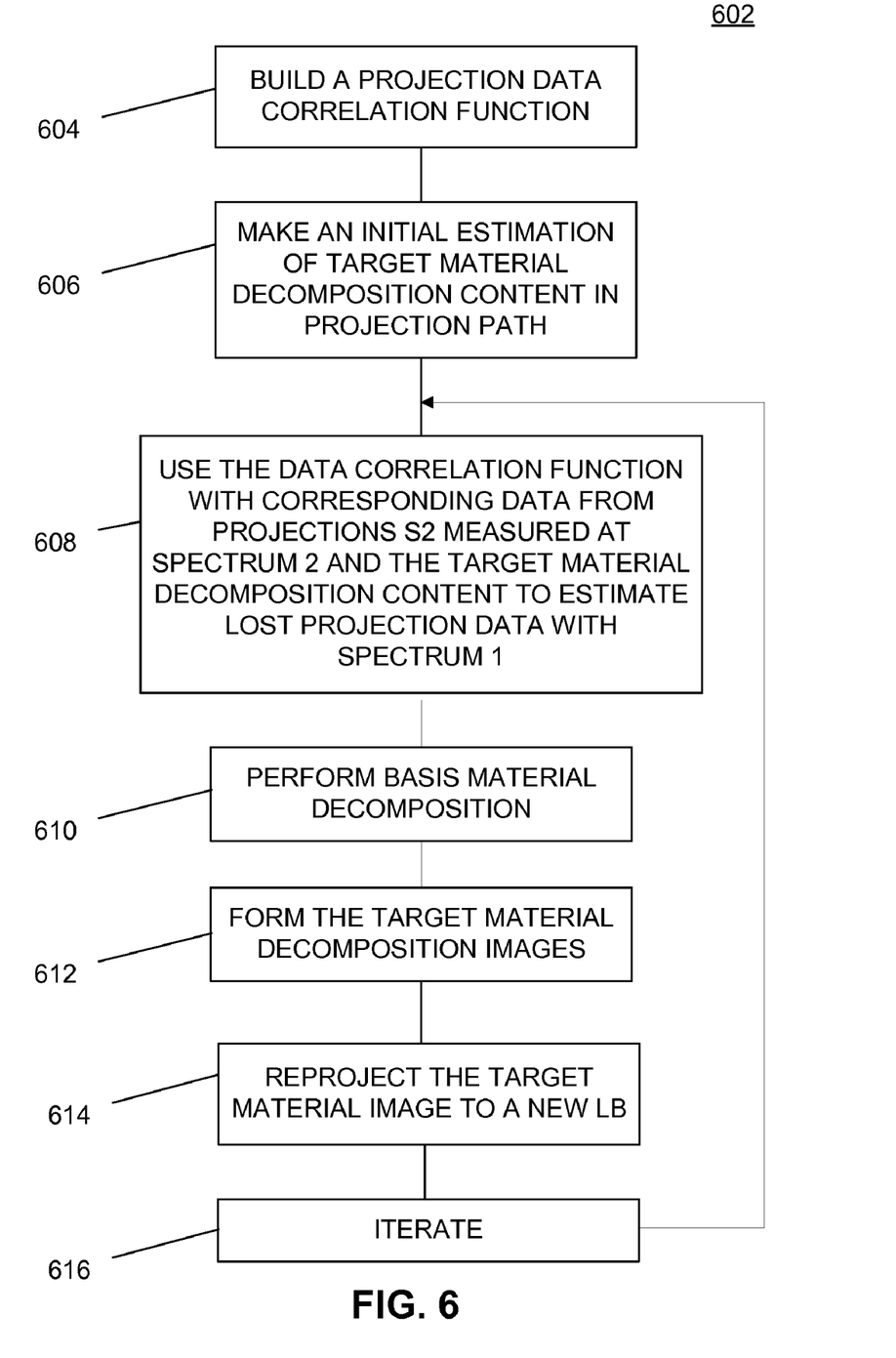
FIG. 6 is a representation of exemplary logic for patching missing projections with partial projections measured at two different incident spectra.

FIG. 6 is a representation of exemplary logic for patching missing projections with partial projections measured at two different incident spectra. STEP 604 builds a projection data correlation function. For example, the correlation function is established between s1-s2. An exemplary approach for capturing an s1/s2 correlation function is now presented, for illustrative purposes. By choosing the basis material as water and bone, dual spectral projections s1 and s2 through various thickness of the basis materials of water (Lwater) and bone (Lb) are computed (e.g., simulation) or measured (e.g., system calibration), resulting in a number of data sets (Lwater, Lb, s1, s2), where s1 can be expressed as a function of data pair (s2, Lb). Data pair (s2, Lb) is fit to s1 with polynomial terms or other functional forms. In an example, fourth order polynomials may be employed. In another example, a lookup table is built from the correlation of s1 to the data pair (s2, Lb).

STEP 606 makes an initial estimation of the decomposition content in the projection path of a target material. The material may comprise any material and/or one specific material type used in the decomposition. For example, the material may comprise bone. STEP 608 uses the data correlation function with corresponding data from projections s2 measured at spectrum 2 and the target material decomposition content to estimate lost projection data with spectrum 1. s1 may be obtained using the correlation function s1=F(s2, Lb). As will be appreciated by those skilled in the art, s1=s2 if Lb=0, since s1 and s2 are the projections corrected with proper spectral calibration. The spectral calibration in an example may be referred to as "water calibration," where s1 and s2 are both linearized to the thickness of water. Lb may be estimated by clipping the s2 image for the target material and forward-projecting the clipped image. In exemplary clipping, pixels in the image with a value smaller than a pre-set value are set to zero. The new projections are applied with a proper scaling factor to form the initial estimated bone density integration Lb.

STEP 610 performs basis material decomposition (BMD). For example, BMD can be is built based on (s1, s2), or (p1, p2), for example, due to the fact that there is a one-to-one mapping between (s1, s2) and (p1, p2). For example, BMD be performed using (s1, s2) to obtain the density projection of target material. STEP 612 forms the target material decomposition images, which are reconstructed from BMD generated projections based on dual spectral projections (s1, s2). One may refer to this exemplary approach as "projection-space BMD". The images also may be obtained with BMD operated based on the two images reconstructed from projections s1 and s2. One may refer to this additional exemplary approach as "image-space BMD". STEP 614 reprojects the target material image to a new Lb. STEP 616 in an example iterates from STEP 608 to STEP 614 a few times. An exemplary study found that two to three iterations were sufficient for most of the systems investigated.

An exemplary implementation recovering missing projection data in an energy discrimination computed tomography (EDCT) system. An exemplary algorithm may be applied to a variety of dual x-ray spectrum systems that have missing data. An exemplary approach obtains EI readout of the projection simultaneously with the ED readout, or in the absence of the ED readout. The readout from the EI detector may be used to patch the corresponding projections in any individual ED energy bin, where the ED detection saturates.

An exemplary implementation patches missing data in one of the two projections corresponding to the same projection path, but acquired at different incident energy spectra. In an exemplary conventional dual-energy imaging, all the pairs of the projections with different incident x-ray spectra have to be present at the same time in order to have the benefits for the dual-energy imaging. An exemplary implementation employs the correlation function between the two projections acquired at different spectra, and the fact the majority of the projection paths have valid projections data from both spectra, to effectively patch the missing data in one of the dual-energy projections, and to enable material decomposition for the imaging system with missing projection data.

An exemplary approach recovers missing data in a CT system, where multiple-spectrum projections are measured for obtaining material composition. An exemplary ED/EI system can produce multiple-spectrum projections and the exemplary ED/EI system may at times have missing data. An exemplary approach provides data recovery for a high frequency electromagnetic energy system with projections measured at multiple spectra of high frequency electromagnetic energy.

Figure 7:
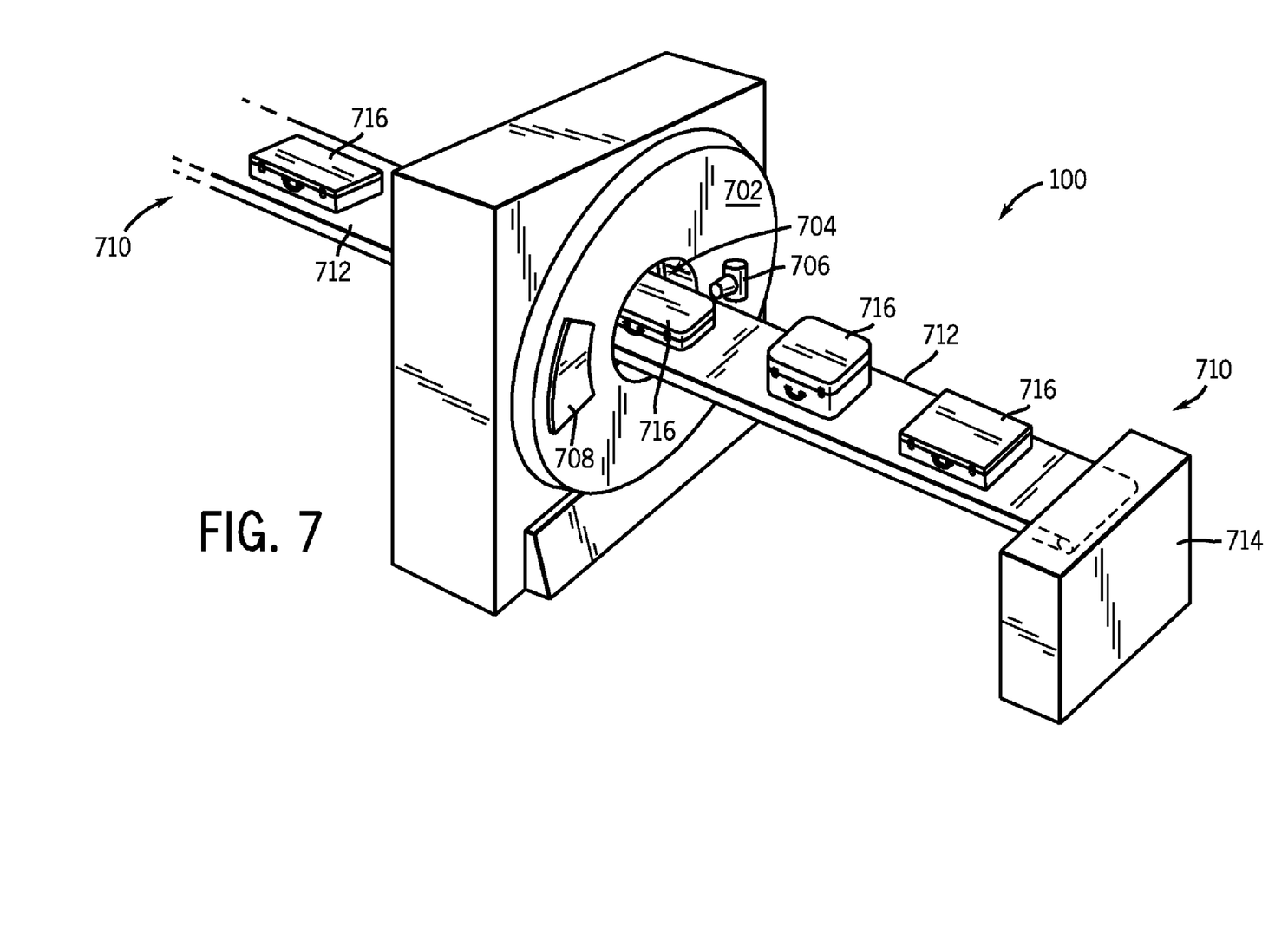
FIG. 7 is a pictorial view of a CT system for use with a non-invasive package inspection system.

Referring now to FIG. 7, package/baggage inspection system 100 includes a rotatable gantry 702 having an opening 704 therein through which packages or pieces of baggage may pass. The rotatable gantry 702 houses an x-ray and/or high frequency electromagnetic energy source 706 as well as a detector assembly 708 having scintillator arrays comprised of scintillator cells. A conveyor system 710 is also provided and includes a conveyor belt 712 supported by structure 714 to automatically and continuously pass packages or baggage pieces 716 through opening 704 to be scanned. Objects 716 are fed through opening 704 by conveyor belt 712, imaging data is then acquired, and the conveyor belt 712 removes the packages 716 from opening 704 in a controlled and continuous manner. As a result, postal inspectors, baggage handlers, and other security personnel may non-invasively inspect the contents of packages 716 for explosives, knives, guns, contraband, etc.

An exemplary implementation comprises one or more high frequency electromagnetic energy sources 14 that emit one or more beams of high frequency electromagnetic energy 16 toward an object 22 to be imaged. A detection assembly 18 is capable of measuring a plurality of projection data at a same projection path that corresponds to a plurality of distinct incident energy spectra. The detection assembly 18 comprises one or more energy discriminating (ED) detectors 302 and/or one or more energy integration (EI) detectors 304 that receive high frequency electromagnetic energy emitted by the one or more high frequency electromagnetic energy sources 14. A data acquisition system (DAS) 32 is operably connected to the one or more ED detectors 302 and/or the one or more EI detectors 304. A computer 36 is operably connected to the DAS 32.

Among the plurality of projection data at the same projection path, at least one of the projection data that corresponds to a particular incident energy spectrum of the plurality of distinct incident energy spectra is valid regardless whether obtained with an ED detector 302 of the one or more ED detectors 302 or an EI detector 304 of the one or more of EI detectors 304. An ED detector 302 of the one or more ED detectors 302 and an EI detector 304 of the one or more EI detectors 304 are substantially adjacent and coextensive for receipt of a beam of high frequency electromagnetic energy 16 of the one or more beams of high frequency electromagnetic energy 16. An ED detector 302 of the one or more ED detectors 302 and an EI detector 304 of the one or more EI detectors 304 perform substantially simultaneous measurements of a beam of high frequency electromagnetic energy 16 of the one or more beams of high frequency electromagnetic energy 16.

An ED detector 302 of the one or more ED detectors 302 filters a low energy part of a beam of high frequency electromagnetic energy 16 of the one or more beams of high frequency electromagnetic energy 16 before an EI detector 304 of the one or more EI detectors 304 receives the beam of high frequency electromagnetic energy 16. The computer 36 is programmed to spectrally correct logged projections from a high frequency electromagnetic energy spectrum received by an ED detector 302 of the one or more ED detectors 302 in a pre-determined energy bin, or by an EI detector 304 of the one or more EI detectors 304. The computer 36 is programmed to determine spectrally corrected logged projections from a high frequency electromagnetic energy spectrum received by an ED detector 302 of the one or more ED detectors 302 and a high frequency electromagnetic energy spectrum received by an EI detector 304 of the one or more EI detectors 304. The computer 36 is programmed to perform basis material decomposition (BMD) for the object 22 to be imaged based on the spectrally corrected logged projections at two distinct incident spectra.

An exemplary implementation comprises a detection assembly 18 capable of measuring a plurality of projection data at a same projection path that corresponds to a plurality of distinct incident energy spectra. The detection assembly 18 comprises one or more energy discriminating (ED) detectors 302 and/or one or more energy integration (EI) detectors 304 that receive high frequency electromagnetic energy emitted by one or more high frequency electromagnetic energy sources 14 that emit one or more beams of high frequency electromagnetic energy 16 toward an object 22 to be imaged. A data acquisition system (DAS) 32 is operably connected to the one or more ED detectors 302 and/or the one or more EI detectors 304. A computer 36 is operably connected to the DAS 32 and programmed to: patch missing data of the plurality of projection data at the same projection path in an incident energy spectrum of the plurality of distinct incident energy spectra. The computer 36 is programmed to patch the missing data through employment of a correlation function between two or more projections acquired at different spectra.

The computer 36 is programmed to determine spectrally corrected logged projections from a high frequency electromagnetic energy spectrum received by an ED detector 302 of the one or more ED detectors 302 and a high frequency electromagnetic energy spectrum received by an EI detector 304 of the one or more EI detectors 304. The computer 36 is programmed to establish a projection data correlation function between the spectrally corrected logged projections at the same projection path with different incident energy spectra. The computer 36 is programmed to employ a logged projection and a BMD density projection that corresponds to a specific material as input to the projection data correlation function.

The computer 36 is programmed to obtain the BMD density projection by: clipping a reconstructed CT image with projections at one incident spectra, or with majority of projections at one incident energy spectrum and a minority of projections at a different incident energy spectrum to obtain a clipped image; and forward-projecting the clipped image to form projections for the specific material.

The computer 36 is programmed to employ the projection data correlation function with inputs of projection data of the plurality of projection data at the same projection path in an energy spectrum of the plurality of distinct incident energy spectra and the BMD density projection that corresponds to the specific material to compute missing projection data in another energy spectrum of the plurality of distinct incident energy spectra for data recovery. The computer 36 is programmed to correct the missing projection data to cause the missing projection data to join smoothly existing projection data in a projection space for the same projection path.

The computer 36 is programmed to, after obtaining substantially all missing projection data at one energy spectrum through employment a correlation function, apply a BMD algorithm to data pairs at two distinct incident energy spectra to obtain an initial set of projections corresponding to a specific material density. The computer 36 is programmed to employ the initial set of projections corresponding to the specific material density to reconstruct an image of the object 22. The computer 36 is programmed to forward project the image of the object 22 to form a new set of projections of the specific material density. The computer 36 is programmed to recover the missing data through employment of the new set of projections in place of the initial set of projections. The computer 36 is programmed to iterate at least two times through obtaining values for the initial set of projections and the new set of projections.

An exemplary implementation comprises a detection assembly 18 capable of measuring a plurality of projection data at a same projection path that corresponds to a plurality of distinct incident energy spectra. The detection assembly 18 comprises one or more energy discriminating (ED) detectors 302 and/or one or more energy integration (EI) detectors 304 that receive high frequency electromagnetic energy emitted by one or more high frequency electromagnetic energy sources 14 that emit one or more beams of high frequency electromagnetic energy 16 toward an object 22 to be imaged. A data acquisition system (DAS) 32 is operably connected to the one or more ED detectors 302 and/or the one or more EI detectors 304. A computer 36 is operably connected to the DAS 32 and programmed to: patch missing data of the plurality of projection data at the same projection path in an incident energy spectrum of the plurality of distinct incident energy spectra. The computer 36 is programmed to patch missing data of the plurality of projection data at the same projection path through employment of a correlation function between two or more projections acquired at different spectra.

An implementation of the system 10 and/or 100 in an example comprises a plurality of components such as one or more of electronic components, hardware components, and/or computer software components. A number of such components can be combined or divided in an implementation of the system 10 and/or 100. An exemplary component of an implementation of the system 10 and/or 100 employs and/or comprises a set and/or series of computer instructions written in or implemented with any of a number of programming languages, as will be appreciated by those skilled in the art. An implementation of the system 10 and/or 100 in an example comprises any (e.g., horizontal, oblique, or vertical) orientation, with the description and figures herein illustrating an exemplary orientation of an implementation of the system 10 and/or 100, for explanatory purposes.

An implementation of the system 10 and/or the system 100 in an example encompasses an article. The article comprises one or more computer-readable signal-bearing media. The article comprises means in the one or more media for desirable functionality.

An implementation of the system 10 and/or the system 100 in an example employs one or more computer readable signal bearing media. A computer-readable signal-bearing medium in an example stores software, firmware and/or assembly language for performing one or more portions of one or more implementations. An example of a computer-readable signal bearing medium for an implementation of the system 10 and/or the system 100 comprises the recordable data storage medium of the image reconstructor 34, and/or the mass storage device 38 of the computer 36. A computer-readable signal-bearing medium for an implementation of the system 10 and/or the system 100 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 100, for instance, one or more of a telephone network, a local area network ("LAN"), a wide area network ("WAN"), the Internet, and/or a wireless network.

The steps or operations described herein are examples. There may be variations to these steps or operations without departing from the spirit of the invention. For example, the steps may be performed in a differing order, or steps may be added, deleted, or modified The present invention has been described in terms of the preferred embodiment, and it is recognized that equivalents, alternatives, and modifications, aside from those expressly stated, are possible and within the scope of the appending claims.

What is claimed is:

1. A CT system, comprising:

a detection assembly capable of measuring a plurality of projection data at a same projection path that corresponds to a plurality of distinct incident energy spectra, wherein the detection assembly comprises one or more energy discriminating (ED) detectors and/or one or more energy integration (EI) detectors that receive high frequency electromagnetic energy emitted by one or more high frequency electromagnetic energy sources that emit one or more beams of high frequency electromagnetic energy toward an object to be imaged;

a data acquisition system (DAS) operably connected to the one or more ED detectors and/or the one or more EI detectors; and a computer operably connected to the DAS and programmed to:

patch missing data of the plurality of projection data at the same projection path in an incident energy spectrum of the plurality of distinct incident energy spectra.

2. The CT system of claim 1, wherein the computer is programmed to patch the missing data through employment of a correlation function between two or more projections acquired at different spectra.

3. The CT system of claim 1, wherein the computer is programmed to determine spectrally corrected projections from a high frequency electromagnetic energy spectrum received by an ED detector of the one or more ED detectors and a high frequency electromagnetic energy spectrum received by an EI detector of the one or more EI detectors;
  wherein the computer is programmed to establish a projection data correlation function between the spectrally corrected projections at the same projection path with different incident energy spectra;
  wherein the computer is programmed to employ a projection and a BMD density projection that corresponds to a specific material as input to the projection data correlation function.

4. The CT system of claim 3, wherein the computer is programmed to obtain the BMD density projection by:
  clipping a reconstructed CT image with projections at one incident spectra, or with majority of projections at one incident energy spectrum and a minority of projections at a different incident energy spectrum to obtain a clipped image; and
  forward-projecting the clipped image to form projections for the specific material.

5. The CT system of claim 3, wherein the computer is programmed to employ the projection data correlation function with inputs of projection data of the plurality of projection data at the same projection path in an energy spectrum of the plurality of distinct incident energy spectra and the BMD density projection that corresponds to the specific material to compute missing projection data in another energy spectrum of the plurality of distinct incident energy spectra for data recovery.

6. The CT system of claim 5, wherein the computer is programmed to correct the missing projection data to cause the missing projection data to join smoothly existing projection data in a projection space for the same projection path.

7. The CT system of claim 1, wherein the computer is programmed to, after obtaining substantially all missing projection data at one energy spectrum through employment a correlation function, apply a BMD algorithm to data pairs at two distinct incident energy spectra to obtain an initial set of projections corresponding to a specific material density.

8. The CT system of claim 7, wherein the computer is programmed to employ the initial set of projections corresponding to the specific material density to reconstruct an image of the object.

9. The CT system of claim 8, wherein the computer is programmed to forward project the image of the object to form a new set of projections of the specific material density.

10. The CT system of claim 9, wherein the computer is programmed to recover the missing data through employment of the new set of projections in place of the initial set of projections.

11. The CT system of claim 10, wherein the computer is programmed to iterate at least two times through obtaining values for the initial set of projections and the new set of projections.

12. A CT system, comprising:
  a detection assembly capable of measuring a plurality of projection data at a same projection path that corresponds to a plurality of distinct incident energy spectra, wherein the detection assembly comprises one or more energy discriminating (ED) detectors and/or one or more energy integration (EI) detectors that receive high frequency electromagnetic energy emitted by one or more high frequency electromagnetic energy sources that emit one or more beams of high frequency electromagnetic energy toward an object to be imaged;
  a data acquisition system (DAS) operably connected to the one or more ED detectors and/or the one or more EI detectors; and
  a computer operably connected to the DAS and programmed to:
  patch missing data of the plurality of projection data at the same projection path through employment of a correlation function between two or more projections acquired at different spectra.

* * * * *